United States Patent [19]

Olejnik et al.

[11] Patent Number: 5,597,559

[45] Date of Patent: Jan. 28, 1997

[54] OPHTHALMIC FORMULATION

[75] Inventors: Orest Olejnik, Trabuco Canyon, Calif.; Fred W. Wendel, Asheboro, N.C.

[73] Assignee: Ciba Geigy Corporation, Tarrytown, N.Y.

[21] Appl. No.: 329,808

[22] Filed: Oct. 26, 1994

Related U.S. Application Data

[63] Continuation-in-part of Ser. No. 152,119, Nov. 12, 1993, abandoned.

[51] Int. Cl.$^6$ ............... A61K 31/765; A61K 9/08
[52] U.S. Cl. .................................................. 424/78.04
[58] Field of Search ............................................. 424/78.04

[56] References Cited

U.S. PATENT DOCUMENTS

| | | | |
|---|---|---|---|
| 3,767,788 | 10/1973 | Rankin | 424/78.04 |
| 4,343,787 | 8/1982 | Katz | 424/428 |
| 4,409,205 | 10/1983 | Shively | 424/78.04 |
| 4,421,748 | 12/1983 | Trager et al. | 514/78 |
| 4,525,346 | 6/1985 | Stark | 424/78.04 |
| 4,914,088 | 4/1990 | Glonek et al. | 514/76 |
| 4,923,699 | 5/1990 | Kaufman | 424/427 |
| 5,072,392 | 7/1991 | Varma | 514/725 |
| 5,174,988 | 12/1992 | Mautone et al. | 424/45 |
| 5,380,303 | 1/1995 | Holly et al. | 604/290 |

FOREIGN PATENT DOCUMENTS

| | | | |
|---|---|---|---|
| 198490 | 10/1986 | European Pat. Off. | A61K 9/08 |
| 244315 | 4/1987 | European Pat. Off. | A61K 9/08 |
| 2169508 | 7/1986 | United Kingdom | A61K 9/08 |
| 93/21903 | 11/1993 | WIPO | A61K 9/00 |

OTHER PUBLICATIONS

Abstract of EP 473159 WPI Mar. 1992 Oshio et al.
Yassa, Dawoud, "Suspension containing Steroids", Journal, p. 422.
Yamamoto, Yujiro, "High–viscosity liquid for protection during surgery".
Search Report dated Aug. 13, 1993: Patents on Lubricating Eye Drops or Artificial Tears.
Equivalents Search dated Aug. 17, 1993.
Moneva et al., "Study of gel formation in solutions of polyvinyl alcohol containing boric acid", Colloid Jnl. of USSR #1, vol. 52, pp. 132–135 (1990).

*Primary Examiner*—Peter F. Kulkosky
*Attorney, Agent, or Firm*—Edward McC. Roberts; R. Scott Meece; Michael U. Lee

[57] ABSTRACT

A preservative-free ophthalmic composition useful in the treatment of conditions such as dry eye comprising an aqueous solution of hydroxypropyl methylcellulose, polyethylene glycol, dextrose, potassium chloride, boric acid and sodium borate decahydrate.

24 Claims, No Drawings

OPHTHALMIC FORMULATION

This application is a continuation-in-part of Ser. No. 08/152,119, filed on Nov. 12, 1993, now abandoned.

This invention relates to ophthalmic formulations. More particularly, this invention relates to artificial tear formulations which are particularly suitable for the treatment of conditions-such as dry eye syndrome.

BACKGROUND OF THE INVENTION

A diminution of the quantity of tears produced and distributed through the lachrymal ducts or a decrease in the stability of the tear film produced results in a condition of the eye commonly referred to as dry eye or dry eye syndrome. Dry eye is a condition of the eye that usually causes a feeling of discomfort such as ocular dryness, grittiness, burning, soreness or scratching, depending upon the condition of the subject. Many theories have been offered to explain the possible causes of dry eye syndrome including insufficient tear volume, mucous deficiency, evaporative losses from tear film and the inability to produce an adequate tear film. Dry eye syndrome, if allowed to remain untreated and uncorrected, can result in permanent damage to the eye with degradation of the exposed ocular tissues or a breakdown of the corneal tissue necessitating, in extreme cases, corneal transplants. Proposed causes for dry eye syndrome, treatment and symptoms thereof are all described in detail in "The Preocular Tear Film In Health, Disease and Contact Lens Wear", The Dry Eye Institute, Lubbock, Tex., 1986.

The most common treatment for dry eye syndrome involves the alleviation of the symptoms by topical administration of a teas substitute that adds a volume of liquid to the anterior surface of the eye and related adnexa. Typical tear substitute compositions comprise water soluble, aqueous polymer compositions. Examples of such compositions include saline solutions of polyvinyl alcohols, hydroxypropyl methylcellulose or carboxymethylcelluloses. Formulations containing substituted cellulose ethers and hydrophilic polymers impart viscosity to the tear formulation and are currently in use for the treatment of dry eye syndrome.

Compositions used in the treatment of dry eye syndrome typically contain a preservative such as benzalkonium chloride if they are intended for multiple use. Preservative free formulations are known in the art. Such preparations are packaged in unit dose containers which are sterile in the unopened form. However, because of the absence of a preservative, each unit dose must be immediately discarded after the prescribed dose has been instilled into the eye. If the opened container is retained for repeated use, microbial contamination can occur which upon administration to the ocular surface increases the risk of infection. Although the use of preservative agents in formulations for treating conditions such as dry eye syndrome results in the destruction or inhibition of the growth of micro-organisms, their use can also damage the ocular tissue. The toxic effects of preservatives is even more pronounced where chronic treatment is required such as in the treatment of dry eye or glaucoma.

There is a need, therefore, for a preservative free composition for the treatment of conditions of the eye which can be used for multiple dose application without the fear of microbial contamination.

It is an object of the present invention to provide an ophthalmic formulation which can be used as a wetting agent for the treatment conditions of the eye such as of dry eye syndrome.

It is another object of the present invention to provide a preservative-free ophthalmic composition which can be used as a carrier for ophthalmic medicaments for the alleviation of the symptoms of dry eye which is not susceptible to contamination by micro-organisms.

A further object of the invention is to provide a preservative-free ophthalmic composition suitable for multi-dose administration.

DETAILS OF THE INVENTION

This invention relates to a preservative-free ophthalmic formulation capable of multi-dose administration and useful as a wetting agent for the treatment of conditions of the eye such as dry eye syndrome.

Broadly, the present ophthalmic formulation includes (a) about 0.20 to 2.5 weight percent of a polymer selected from the group consisting of hydroxyalkyl cellulosics and polyalkylene glycols; (b) a non-ionic tonicity adjusting agent selected from the group consisting of mannitol, sorbitol, dextrose, sucrose, urea, glycerol, and mixtures thereof, in amount sufficient to generate a tonicity of about 50 to 350 milliosmols per kilogram (mOsmol/kg); (c) an ionic salt selected from the group consisting of alkali metal halides in an amount sufficient to approximate the salt concentration of the human tear fluid; and (d) an antimicrobial in an amount sufficient to generate sufficient borate to maintain or reduce microbial concentrations for a period of 12 hours to 24 hours, more preferably 12 hours to 72 hours.

Preferably, the formulation includes (1) about 0.20 to 2.5 weight percent of a polymer selected from the group consisting of hydroxypropylmethyl cellulose, hydroxyethylmethyl cellulose, hydroxypropyl cellulose, carboxymethyl cellulose, and mixtures thereof. More preferably, the formulation includes (1) about 0.10 to 0.50 weight percent of the hydroxyalkyl cellulosic and (2) about 0.50 to 2.0 weight percent of a polyalkylene glycol selected from the group consisting of polypropylene glycol and polyethylene glycol. An even more preferred composition includes 0.20 to 0.30 weight percent hydroxypropylmethyl cellulose and 0.50 to 2.0 weight percent polyethylene glycol.

The tonicity adjusting agent is preferably present in an amount from about 0.01 to 0.10 weight percent. A preferred tonicity adjusting agent is dextrose.

The ionic salt is preferably selected from the group consisting of sodium chloride, potassium chloride, zinc chloride, calcium chloride, and mixtures thereof. A preferred formulation includes about 0.01 to 0.50 weight percent ionic salt, more preferably, potassium chloride. An even more preferred formulation includes 0.01 to 0.30 weight percent potassium chloride.

The antimicrobial capable of generating borate in solution may be selected from the group consisting of boric acid, sodium borate, and mixtures thereof. Preferably, the antimicrobial is a mixture of boric acid and sodium borate. The weight percentage of antimicrobial is preferably sufficient to generate 0.05 to 3 weight percent borate in solution, more preferably sufficient to generate about 0.10 to 2.0% borate in solution. A particularly preferred formulation includes about 0.05 to 2.0 weight percent boric acid and 0.01 to 0.20 weight percent sodium borate.

Thus, a preferred formulation of the present invention is comprised of an aqueous solution containing from about 0.20 to about 0.30 percent weight/volume of hydroxypropyl methylcellulose, from about 0.5 to about 2.0 percent weight/ volume of polyethylene glycol, from about 0.01 to about 0.10 percent weight/volume of dextrose, from about 0.01 to about 0.20 percent weight/volume of potassium chloride, from about 0.05 to about 2.0 percent weight/volume of boric acid and from about 0.01 to about 0.20 percent weight/volume of sodium borate. Purified water is added to the formulation to bring the total to 100%.

In a preferred embodiment of the invention, the ophthalmic formulation comprises 0.25% (w/v) hydroxypropyl methylcellulose, 1.0% (w/v) polyethylene glycol, 0.05% (w/v) anhydrous dextrose, 0.14% (w/v) potassium chloride, 1.18% (w/v) boric acid and 0.12% (w/v) sodium borate decahydrate. Purified water is added to bring the total to 100%.

Buffers are used in ophthalmic solutions to maintain their proper pH. Since tears have a pH of approximately 7.4, it is generally accepted as the ideal pH for ophthalmic preparations except in those situations where a higher or lower pH is indicated to optimize the stability of one of the other ingredients in the preparation. Borate buffers such as boric acid combined with sodium borate are commonly used in ophthalmic preparations and may even lead to improved comfort for the user. Borate buffers are used in commercially available ophthalmic preparations used to treat dry eye syndrome.

Houlsby et al demonstrated the lack of survival or proliferation of certain microorganisms in a borate-buffer vehicle [Houlsby, R. D. et al. Antimicrobial Activity of Borate-Buffered solutions, Antimicrobial Agents and Chemotherapy, p. 803–806, vol. 29, No. 5 (1986)]. In the formulation of the present invention the borate buffered system is suitable for use as a vehicle for obtaining a stable preservative-free clear colorless solution.

Polyethylene glycol 400 is a water soluble polymer of ethylene oxide and water which is commonly used in pharmaceutical and cosmetic preparations as dispersants and emulsifying agents. Hydroxypropyl methylcellulose is employed as a thickening agent to keep the liquid in contact with the eye surface for as long as possible.

The ophthalmic formulation of the present invention can be formulated as a clear, colorless stable solution which is preservative free and can be used for multi-dose administration in the treatment of conditions of the eye such as dry eye syndrome.

The ideal pH of the solution is in the range of 7.0–7.5. The solution is preferably a hypotonic solution. The preferred pH is 7.3.

Variations within or without the above percent ranges for the components of the ophthalmic vehicle solution can be made based on evaluation techniques known in the art. For example, gamma scintigraphy has been used to monitor the ocular distribution of solutions and the effect of polymers on the pre-corneal drainage of the solutions (C. G. Wilson et al. Journal of Pharmacol., Vol. 35, pp. 451–454 (1983).

The method of preparing the ophthalmic solution of the present invention requires that a dispersion of the hydroxypropyl methylcellulose (HPMC) be prepared prior to the addition of the buffer solution. The HPMC dispersion is prepared in a suitable vessel such as a volumetric flask or, when larger amounts are desired, in a jacketed pressure tank by the addition of the HPMC to purified water which has been preheated to about 80°–90° C. The dispersion is then sterilized at a temperature between about 118°–123° C. by a suitable means such as an autoclave or, in the case of larger preparations, by passing steam through the jacket of the pressure tank at a temperature between about 118°–123° C. and a pressure of about 20–25 psi. The sterilization process is continued for about 35–45 minutes. The buffer solution is prepared by combining the sodium borate, boric acid, polyethylene glycol 400, potassium or sodium chloride and dextrose in a suitable vessel. The HPMC dispersion and the buffer solution are each cooled to about 15°–20° C. The buffer solution is then sterilized by aseptically filtering it through a sterile validated 0.2 micron cartridge filter into the sterile HPMC solution, preferably at a slow rate. The resulting mixture is thoroughly mixed to obtain the preservative-free ophthalmic solution of the present invention. The volume, if necessary, is adjusted and the pH, if necessary, is adjusted to about 7.0–7.5 with a suitable base or acid such as sodium hydroxide or hydrochloric acid. The product can then be aseptically filled into blow molded unit containers which can be sealed until ready to be used.

The resulting solution is stable, and after sterilization, it can be packaged, stored and used directly. Application will be in drop form in the manner typically used to apply eye drops. The normal squeeze-type liquid drop application devices are perfectly suited for use in applying the ophthalmic solution. Use of the artificial tear composition is conveniently effected by instilling the composition dropwise into the affected eye of the user.

The formulations of the present invention are especially advantageous for use in multi-dose containers. Multi-dose containers, as used herein, refer to containers which allow two or more separate applications of the ophthalmic solution present within the container. Such containers are resealable, i.e., the container cap may be removed for a first application, and then the cap may be replaced onto the container, thereby providing a substantially liquid impermeable seal again.

The present formulations are especially advantageous for use in a multi-dose container because the present formulations achieve a remarkable balance of antimicrobial properties with ophthalmic acceptability. In contrast, previously-known ophthalmic dry eye formulations contain either (1) no preservatives or (2) conventional preservatives, such as benzalkonium chloride, sorbic acid, thimerosal, or chlorbutanol. Both of these types of formulations suffer from certain disadvantages.

Those formulations containing no preservative are packaged in a unit dose container, i.e., only a single dose can be provided by a given container. Such preservative-free compositions are subject to uncontrolled microbial growth once the consumer initially breaks the container seal. Accordingly, the consumer is instructed to dispose of the container after the first dose. This results in excessive packaging waste, consumer discomfort, and waste of the remaining solution in the container after a single dose. In addition, the consumer sometimes reuses the solution remaining in the container after storing the container for some hours, in contradiction to the instructions. Such misuse of unit dose containers jeopardizes the consumers' health, because of the possibility of microbial growth in the container.

On the other hand, formulations containing conventional preservatives suffer from another disadvantage. While conventional preservatives typically completely eradicate microorganisms and prevent subsequent microbial growth, such preservatives are too potent for direct contact with the eye. Thus, conventional preservatives can be harmful to the ocular tissue of the user. Further, conventional preservatives cause patient discomfort, thereby resulting in patient non-compliance with recommended usage instructions. Accordingly, there is an increasing number of commercial dry eye formulations which are of the single-use or unit dose type, as opposed to the conventional preservative multi-dose type.

Remarkably, the present invention offers a third alternative. The present formulations inhibit microbial growth for a limited period of time, without causing damage or discomfort to the consumer or patient. This limited period of microorganism growth inhibition is at least 12 hours, preferably 12 to 24 hours, and more preferably, 12 to 72 hours. While microorganisms are not entirely killed with the present formulation, the growth is inhibited for a limited period. Thus, the present formulations can be exposed to the environment, by the consumer breaking the container-cap seal, for a period of at least 12 hours without disadvantageous microbial growth or consumer discomfort. Hence, the present multi-dose formulations offer advantages in reducing production expense and consumer costs, reducing packaging waste, and improving consumer comfort, compliance, and health.

The compositions of the present invention, when instilled dropwise in the eye, swell the tear meniscus and, with normal blinking, the tear meniscus becomes thoroughly admixed with the tear film. The flooded tear meniscus returns to its steady-state size and the superficial lipid layer is reestablished over the aqueous layer.

The compositions of the present invention do not contribute to hydrophobic contamination of the mucous layer and are capable of forming a hydrophobic layer having all of the functional properties of a normal mucous layer.

In order that those skilled in the art can more fully understand this invention the following example of preparation is set forth. The example is given solely for purposes of illustration and should not be considered as expressing limitations.

EXAMPLE 1

Purified water (300 ml) is added to a 500 ml volumetric flask and the water is heated to 80°–90° C. Hydroxypropyl methylcellulose (HPMC) (0.25 g) is added to and dispersed in the water with constant agitation. The HPMC dispersion is autoclaved at 121° C. for about 45 minutes and then cooled to 15°–20° C. Polyethylene glycol 400 (5.0 g), sodium borate (0.6 g), potassium chloride (0.7 g), boric acid (5.9 g) and dextrose (0.25 g) are combined in 300 ml of purified water and the resulting solution is cooled to 15°–20° C. The cooled buffer solution is then aseptically filtered slowly through a sterile validated 0.2 micron cartridge filter into the agitated sterile HPMC solution. The stirring is continued until the resultant mixture is thoroughly mixed to obtain the sterile preservative-free ophthalmic solution. The pH is adjusted, if necessary, to 7.0–7.5 with a 10% sodium hydroxide solution and the volume is adjusted to 500 ml, if necessary, by the addition of purified water.

| Formula I | | |
|---|---|---|
| Hydroxypropyl Methylcellulose (90HG 4000 COS), USP | 2.5 mg/ml | 0.25% |
| Polyethylene Glycol 400, NF | 10.0 mg/ml | 1.0% |
| Dextrose Anhydrous, USP | 0.5 mg/ml | 0.05% |
| Potassium Chloride, USP | 1.4 mg/ml | 0.14% |
| Boric Acid, NF | 11.8 mg/ml | 1.18% |
| Sodium Borate Decahydrate, NF | 1.2 mg/ml | 0.12% |
| Purified Water, USP | q.s. 1 ml | 100% |
| Formula II | | |
| Boric Acid | 1.18% | 5.9 g. |
| HPMC | 0.25% | 1.25 g. |
| PEG 400 | 1.0% | 5.0 g. |
| Dextrose | 0.05% | 0.25 g. |
| Potassium Chloride | 0.27% | 1.35 g. |
| Sodium Borate Decahydrate | 0.12% | 0.6 g. |
| Purified Water | q.s. to 100% | q.s. to 500 ml. |

The artificial tears formulation was tested for the proliferation of bacterial and fungal microorganisms such as *S. aureus, E. coli, P. aeruginosa, A. niger,* and *C. albicans*. None of the test organisms were found to proliferate in the artificial tears formulation. In general there was a decrease in counts over a seven day test period. *Staphylococcus aureus* and *A. niger* did not proliferate in the tear formulation, however, there was a resurgence in counts for *E. coli, P. aeruginosa* and *C. albicans* by seven days post inoculation.

EXAMPLE 2

An artificial tears formulation is prepared with the following composition, in weight percentages: about 0.25% hydroxypropylmethyl cellulose, about 1.0% polyethylene glycol, about 0.05% dextrose, about 0.14 potassium chloride, about 1.18% boric acid, and about 0.12% sodium borate.

Inoculum formulations are prepared with about $1 \times 10^8$ colony forming units (CFU) per milliliter (ml) with the following microorganisms: *Esherichia coli, Pseudomonas aeruginosa, Staphylococcus aureus, Candida albicans, Aspergillus niger.*

About 20 ml samples of the artificial tears formulation are mixed with about 0.1 ml of each of the inoculum formulations. The resulting bacteria or fungal concentrations are about $10^5$ or $10^6$ CFU/ml. Each of these samples are tested for the microorganism concentration at the time of inoculation, and 2, 4, 6, 16, 24 and 48 hours after inoculation.

The prior procedure is repeated three times, thereby producing three lots of samples, in order to better verify the accuracy of the results. The lots are labeled A, B, and C. The results are reported in TABLES I–V, for *A. niger, C. albicans, S. aureus, P. aeruginosa,* and *E. coli*, respectively.

COMPARATIVE EXAMPLE 3

The procedure of Example 2 is repeated with the substitution of normal saline for the artificial tears formulation. The results are shown in TABLES I–V, adjacent to the results of EXAMPLE 2, lots A–C.

TABLE I

*A. niger*

| SAMPLE | At Inoculation | 2 hours | 4 hours | 6 hours | 16 hours | 24 hours | 48 hours |
|---|---|---|---|---|---|---|---|
| normal saline | $1.9 \times 10^6$ | $2.5 \times 10^6$ | $1.6 \times 10^6$ | $1.1 \times 10^6$ | $1.3 \times 10^6$ | $1.5 \times 10^6$ | $1.0 \times 10^6$ |
| artificial | $1.9 \times 10^6$ | $2.2 \times 10^6$ | $2.0 \times 10^6$ | $9 \times 10^4$ | $1 \times 10^3$ | $1.2 \times 10^3$ | $3.3 \times 10^2$ |

TABLE I-continued

*A. niger*

| SAMPLE | At Inoculation | 2 hours | 4 hours | 6 hours | 16 hours | 24 hours | 48 hours |
|---|---|---|---|---|---|---|---|
| tears Lot A artificial tears Lot B | $1.9 \times 10^6$ | $4.4 \times 10^5$ | $2.5 \times 10^5$ | $1.2 \times 10^5$ | $1.1 \times 10^3$ | $1.2 \times 10^3$ | $3.2 \times 10^2$ |
| artificial tears Lot C | $1.9 \times 10^6$ | $1.3 \times 10^6$ | $1.8 \times 10^6$ | $9 \times 10^5$ | $1.4 \times 10^3$ | $1.6 \times 10^3$ | $1.6 \times 10^2$ |

TABLE II

*C. albicans*

| SAMPLE | At Inoculation | 2 hours | 4 hours | 6 hours | 16 hours | 24 hours | 48 hours |
|---|---|---|---|---|---|---|---|
| normal saline | $1.2 \times 10^6$ | $1.1 \times 10^6$ | $1.2 \times 10^6$ | $1.7 \times 10^6$ | $1.3 \times 10^6$ | $1.4 \times 10^6$ | $8.9 \times 10^5$ |
| artificial tears Lot A | $1.2 \times 10^6$ | $1.0 \times 10^6$ | $1.3 \times 10^6$ | $1.3 \times 10^6$ | $1.8 \times 10^6$ | $1.4 \times 10^6$ | $1.0 \times 10^6$ |
| artificial tears Lot B | $1.2 \times 10^6$ | $1.7 \times 10^6$ | $1.2 \times 10^6$ | $1.5 \times 10^6$ | $1.2 \times 10^6$ | $1.6 \times 10^5$ | $1.2 \times 10^6$ |
| artificial tears Lot C | $1.2 \times 10^6$ | $1.2 \times 10^6$ | $1.6 \times 10^6$ | $1.2 \times 10^6$ | $1.3 \times 10^6$ | $1.4 \times 10^6$ | $1.1 \times 10^6$ |

TABLE III

*S. aureus*

| SAMPLE | At Inoculation | 2 hours | 4 hours | 6 hours | 16 hours | 24 hours | 48 hours |
|---|---|---|---|---|---|---|---|
| normal saline | $9.4 \times 10^5$ | $1.0 \times 10^6$ | $8.4 \times 10^5$ | $7.4 \times 10^5$ | $8.6 \times 10^6$ | $3.6 \times 10^6$ | $3.5 \times 10^5$ |
| artificial tears Lot A | $9.4 \times 10^5$ | $1.1 \times 10^6$ | $9.2 \times 10^5$ | $7.6 \times 10^5$ | $7.2 \times 10^5$ | $8.8 \times 10^5$ | $5.7 \times 10^5$ |
| artificial tears Lot B | $9.4 \times 10^5$ | $1.2 \times 10^6$ | $1.1 \times 10^6$ | $1.1 \times 10^6$ | $8.9 \times 10^5$ | $6.8 \times 10^5$ | $4.8 \times 10^5$ |
| artificial tears Lot C | $9.4 \times 10^5$ | $7.8 \times 10^5$ | $1.5 \times 10^6$ | $1.0 \times 10^6$ | $7.2 \times 10^5$ | $1.3 \times 10^6$ | $7.4 \times 10^5$ |

TABLE IV

*P. aeruginosa*

| SAMPLE | At Inoculation | 2 hours | 4 hours | 6 hours | 16 hours | 24 hours | 48 hours |
|---|---|---|---|---|---|---|---|
| normal saline | $6.4 \times 10^5$ | $5.4 \times 10^5$ | $7.3 \times 10^5$ | $1.1 \times 10^6$ | $7.6 \times 10^5$ | $1.5 \times 10^6$ | $5.1 \times 10^6$ |
| artificial tears Lot A | $6.4 \times 10^5$ | $5.5 \times 10^5$ | $6.3 \times 10^5$ | $7.0 \times 10^5$ | $7.4 \times 10^5$ | $8.0 \times 10^5$ | $4.7 \times 10^5$ |
| artificial tears Lot B | $6.4 \times 10^5$ | $1.0 \times 10^6$ | $5.7 \times 10^5$ | $9.5 \times 10^5$ | $7.3 \times 10^5$ | $6.3 \times 10^5$ | $6.4 \times 10^5$ |
| artificial tears Lot C | $6.4 \times 10^5$ | $5.4 \times 10^5$ | $7.1 \times 10^5$ | $7.3 \times 10^5$ | $6.8 \times 10^5$ | $8.2 \times 10^5$ | $4.6 \times 10^5$ |

TABLE V

*E. coli*

| SAMPLE | At Inoculation | 2 hours | 4 hours | 6 hours | 16 hours | 24 hours | 48 hours |
|---|---|---|---|---|---|---|---|
| normal saline | $1.2 \times 10^6$ | $1.1 \times 10^6$ | $1.0 \times 10^6$ | $8.1 \times 10^5$ | $7.6 \times 10^5$ | $8.3 \times 10^5$ | $7.1 \times 10^5$ |
| artificial tears Lot A | $1.2 \times 10^6$ | $9.8 \times 10^5$ | $8.8 \times 10^5$ | $9.0 \times 10^5$ | $8.8 \times 10^5$ | $6.7 \times 10^5$ | $5.5 \times 10^5$ |
| artificial tears Lot B | $1.2 \times 10^6$ | $9.9 \times 10^5$ | $1.4 \times 10^6$ | $1.3 \times 10^6$ | $6.6 \times 10^5$ | $8.1 \times 10^5$ | $5.7 \times 10^5$ |

TABLE V-continued

E. coli

| SAMPLE | At Inoculation | 2 hours | 4 hours | 6 hours | 16 hours | 24 hours | 48 hours |
|---|---|---|---|---|---|---|---|
| artificial tears Lot C | $1.2 \times 10^6$ | $8.1 \times 10^5$ | $1.6 \times 10^5$ | $7.1 \times 10^5$ | $1.2 \times 10^6$ | $8.0 \times 10^5$ | $3.9 \times 10^5$ |

The results shown in TABLES I–V illustrate that the present artificial tears solution either inhibits growth or proliferation of microorganisms, and at times, reduces microorganism concentrations, for a period of up to 48 hours. The five microorganisms studied are those which have prime importance in ophthalmic applications.

The results are especially important in the use of the present artificial tears formulations for multi-dose containers. The re-use of the present artificial tears solution from a container opened within 48 hours from the final use clearly does not endanger the user, since the microorganisms are held essentially at the original inoculation levels. Thus, if the formulation became directly or indirectly contaminated by external microorganisms during use by the consumer, the consumer would not be expected to be at any substantially greater risk of infection than if the formulation were preserved with conventional preservatives, and moreover, the consumer would be at a significantly reduced risk when compared to unpreserved formulations. On the other hand, the boric acid/sodium borate system does not present the toxic side-effects of conventional preservatives, such as benzalkonium chloride.

EXAMPLE 4

The three lots of artificial tear formulations of EXAMPLE 2 are used for the present Example.

Inoculum formulations are prepared with about $2 \times 10^3$ to $2 \times 10^4$ colony forming units CFU/ml with the following microorganisms: E. coli, P. aeruginosa, S. aureus, C. albicans, A. niger.

About 20 ml samples of the artificial tears formulation are mixed with about 0.1 ml of each of the inoculum formulations. The resulting bacteria or fungal concentrations are about $10^5$ or $10^6$ CFU/ml. Each of these samples are tested for the microorganism concentration at the time of inoculation, and 6 hours, 24 hours, 2 days, 4 days, and 7 days after inoculation.

The results are reported in TABLES VI–X, for A. niger, C. albicans, S. aureus, P. aeruginosa, and E. coli, respectively. The numerical results are expressed in CFU/ml.

TABLE VI

A. niger

| SAMPLE | At Inoculation | 6 hours | 1 day | 2 days | 4 days | 7 days |
|---|---|---|---|---|---|---|
| artificial tears Lot A | 140 | 2 | 0 | 1 | 0 | 0 |
| artificial tears Lot B | 140 | 0 | 1 | 0 | 0 | 0 |
| artificial tears Lot C | 140 | 0 | 2 | 0 | 0 | 0 |

TABLE VII

C. albicans

| SAMPLE | At Inoculation | 6 hours | 1 day | 2 days | 4 days | 7 days |
|---|---|---|---|---|---|---|
| artificial tears Lot A | 120 | 130 | 99 | 52 | 35 | 0 |
| artificial tears Lot B | 120 | 99 | 89 | 47 | 13 | 0 |
| artificial tears Lot C | 120 | 99 | 63 | 63 | 16 | 0 |

TABLE VIII

S. aureus

| SAMPLE | At Inoculation | 6 hours | 1 day | 2 days | 4 days | 7 days |
|---|---|---|---|---|---|---|
| artificial tears Lot A | 510 | 540 | 320 | 59 | 0 | 0 |
| artificial tears Lot B | 510 | 61 | 88 | 0 | 0 | 0 |
| artificial tears Lot C | 510 | 58 | 52 | 55 | 0 | 0 |

TABLE IX

P. aeruginosa

| SAMPLE | At Inoculation | 6 hours | 1 day | 2 days | 4 days | 7 days |
|---|---|---|---|---|---|---|
| artificial tears Lot A | 490 | 380 | 190 | 110 | 0 | 0 |
| artificial tears Lot B | 490 | 280 | 190 | 110 | 0 | 0 |
| artificial tears Lot C | 490 | 320 | 360 | 200 | 160 | 95 |

TABLE X

E. coli

| SAMPLE | At Inoculation | 6 hours | 1 day | 2 days | 4 days | 7 days |
|---|---|---|---|---|---|---|
| artificial tears Lot A | 370 | 320 | 97 | 74 | 16 | 13 |
| artificial tears Lot B | 370 | 180 | 96 | 55 | 34 | 22 |
| artificial tears Lot C | 370 | 270 | 120 | 98 | 44 | 32 |

The results shown in TABLES VI–X illustrate that the preferred artificial tears formulation of the present invention reduces microorganism concentrations significantly over a 7 day period when the formulation is inoculated with microorganism concentrations on the order of $10^2$–$10^3$ CFU/ml. Thus, the presently preferred formulation is suited to use in a multi-dose container for a limited re-use period, preferably less than about 72 hours.

The invention, in its broader aspects, is not limited to the specific details shown and described and departures may be made from such details without departing from the principles thereof and without sacrificing the chief advantages thereof.

What is claimed is:

1. An preservative-free ophthalmic composition, comprising:
   (a) about 0.20 to 2.5 weight percent of hydroxyalkyl cellulosic; polymer and from about 0.5 to 2.0 weight percent polyalkylene glycol;
   (b) a non-ionic tonicity adjusting agent selected from the group consisting of mannitol, sorbitol, dextrose, sucrose, urea, glycerol, and mixtures thereof, in amount sufficient to generate a tonicity of about 50 to 350 milliosmols per kilogram (mOsmol/kg);
   (c) an ionic salt, selected from the group consisting of alkali metal halides, in an amount sufficient to approximate the salt concentration of the human tear fluid; and
   (d) an antimicrobial in an amount sufficient to generate sufficient borate to maintain or reduce microbial concentrations for a period of 12 hours to 72 hours.

2. An ophthalmic composition of claim 1, wherein said hydroxyalkyl cellulose is selected from the group consisting of hydroxypropylmethyl cellulose, hydroxyethylmethyl cellulose, hydroxypropyl cellulose, carboxymethyl cellulose, and mixtures thereof.

3. An ophthalmic composition of claim 2, comprising 0.10 to 0.50 weight percent of said hydroxyalkyl cellulose and 0.50 to 2.0 weight percent of a polyalkylene glycol selected from the group consisting of polyethylene glycol and polypropylene glycol.

4. An ophthalmic composition of claim 3, comprising 0.20 to 0.30 weight percent hydroxypropymethyl cellulose and 0.50 to 2.0 weight percent polyethylene glycol.

5. An ophthalmic composition of claim 1, comprising 0.01 to 0.10 weight percent of said tonicity agent.

6. An ophthalmic composition of claim 5, wherein said tonicity adjusting agent is dextrose.

7. An ophthalmic composition of claim 1, wherein said ionic salt is selected from the group consisting of sodium chloride, potassium chloride, zinc chloride, calcium chloride, and mixtures thereof.

8. An ophthalmic composition of claim 7, wherein the weight percentage of said ionic salt is 0.01 to 0.50.

9. An ophthalmic composition of claim 8, wherein said ionic salt is potassium chloride and the weight percentage of said salt is 0.01 to 0.30.

10. An ophthalmic composition of claim 1, wherein said antimicrobial is selected from the group consisting of boric acid, sodium borate, and mixtures thereof.

11. An ophthalmic composition of claim 10, wherein said antimicrobial generates 0.05 to 3.0 weight percent borate in solution.

12. An ophthalmic composition of claim 11, wherein said antimicrobial comprises:
    (1) 0.05 to 2.0 weight percent boric acid; and
    (2) 0.01 to 0.20 weight percent sodium borate.

13. An ophthalmic composition of claim 1, comprising:
    (a) about 0.20 to 0.30 weight percent/volume of hydroxypropylmethyl cellulose;
    (b) about 0.50 to 2.0 weight percent/volume of polyethylene glycol;
    (c) about 0.01 to 0.10 weight percent/volume of dextrose;
    (d) about 0.01 to 0.30 weight percent/volume of potassium chloride;
    (e) about 0.05 to 2.0 weight percent/volume of boric acid;
    (f) about 0.01 to 0.20 weight percent/volume sodium borate; and
    (g) the balance water.

14. An ophthalmic composition of claim 13, comprising:
    (a) about 0.25 weight percent hydroxypropylmethyl cellulose;
    (b) about 1.0 weight percent polyethylene glycol;
    (c) about 0.05 weight percent dextrose;
    (d) about 0.14 weight percent potassium chloride;
    (e) about 1.18 weight percent boric acid; and
    (f) about 0.12 weight percent sodium borate.

15. An ophthalmic composition of claim 1, wherein the pH is about 7.0 to 7.5.

16. A method of treating conditions of the eye which comprises topically administering to the ocular environment an effective amount of the composition of claim 1.

17. A method of treating conditions of the eye which comprises topically administering to the ocular environment an effective amount of the ophthalmic composition of claim 8 which is capable of sufficiently inhibiting microorganism growth for period of time sufficient to allow use of the unpreserved preparation repetitively for a period of 12 to 72 hours after exposure of the composition to the surrounding environment, wherein said ophthalmic composition does not cause the consumer substantial discomfort when the composition is directly contacted with the eye.

18. A method of claim 17, wherein said composition includes an borate in an amount sufficient to substantially inhibit microbial growth for a period of 12 to 72 hours.

19. A method of treating dry eye syndrome which comprises topically administering to the eye an effective amount of the composition of claim 1.

20. A method of preparing an ophthalmic composition of claim 1 for the treatment of conditions of the eye which comprises:
    (a) dispersing a hydroxyalkyl cellulose in purified water at an elevated temperature, thereby forming an aqueous dispersion;
    (b) sterilizing the aqueous dispersion at a temperature of about 118° to 123° C.;
    (c) cooling the dispersion to about 15° to 20° C;
    (d) cooling an aqueous buffer solution comprised of a polyethylene glycol, sodium borate, boric acid, potassium chloride, and dextrose to about 15° to 20° C. said destrose being present in an amount perkilogram (mOsmol/kg);
    (e) aseptically adding the buffer solution slowly to the cooled hydroxyalkyl cellulose solution through a sterile cartridge filter with stirring; and
    (f) adjusting the pH to about 7.0 to 7.5.

21. The method of claim 20, wherein the pH is adjusted with a reagent selected from sodium hydroxide and hydrochloric acid.

22. The method of claim 20, wherein the elevated temperature is between 80° and 90° C.

23. A method of preparing an ophthalmic dry eye formulation of claim 8 which includes a polymer selected from hydroxyalkyl cellulosics and polyalkylene glycols, a nonionic tonicity agent, and an ionic salt, said method comprising the step of adding sufficient antimicrobial agent to the formulation, said antimicrobial generating sufficient borate to maintain or reduce the microbial concentration in said formulation over a period of 12 to 72 hours.

24. A method of claim 23, comprising the steps of:
   (a) adding boric acid to said formulation in an amount of 0.05 to 2.0 weight percent; and
   (b) adding sodium borate to said formulation in an amount of 0.01 to 0.20 weight percent.

* * * * *